United States Patent [19]
Walker et al.

[11] Patent Number: 5,330,491

[45] Date of Patent: Jul. 19, 1994

[54] ENDOSCOPIC SUTURING DEVICE

[75] Inventors: Edward E. Walker, Stockton; Royce L. Ferderick, South Bound Brook; C. Ray Britt, South Plainfield; Gene Kammerer, East Brunswick; Barbara Howard, Plainfield, all of N.J.

[73] Assignee: Ethicon, Inc., Somerville, N.J.

[21] Appl. No.: 65,590

[22] Filed: Jun. 7, 1993

Related U.S. Application Data

[63] Continuation-in-part of Ser. No. 947,662, Sep. 18, 1992, Pat. No. 5,234,445.

[51] Int. Cl.$^5$ ............................................. A61B 17/00
[52] U.S. Cl. ..................................... 606/148; 606/139
[58] Field of Search ................... 606/1, 113, 145, 148, 606/144, 113

[56] References Cited

U.S. PATENT DOCUMENTS

| | | | |
|---|---|---|---|
| 2,012,776 | 8/1935 | Roeder | 606/139 |
| 4,177,813 | 12/1979 | Miller | 606/139 |
| 5,144,961 | 9/1992 | Chen et al. | 606/139 |
| 5,152,769 | 10/1992 | Baber | 606/139 |
| 5,211,650 | 5/1993 | Noda | 606/148 |

*Primary Examiner*—Stephen C. Pellegrino
*Assistant Examiner*—Gary Jackson
*Attorney, Agent, or Firm*—Emil Richard Skula

[57] ABSTRACT

A medical device for ligation or approximating tissue is disclosed. The device has a cannula with proximal and distal ends. The distal end of the cannula has a beveled surface, and the cannula has first and second channels, the first channel extending axially through it, and the second channel extending from the beveled surface to the first channel. The device includes a suture with a slide end and a distal loop, as well as a slip knot securing the loop to the slide end. The slide end is threaded thorough the first and second channels of the cannula and it protrudes from the proximal end of the cannula. In addition, the device incorporates means for securing the positioning of the slide end of the suture in the first channel of the cannula. The device may optionally have a frangible proximal end wherein the proximal end of the suture is mounted to the frangible proximal end.

The device is particularly well adapted for use during endoscopic surgery when it is necessary to perform operative procedures through small openings in the body. The device is easy to maneuver and to position, and does not require the user to make the suture knot outside the body.

9 Claims, 9 Drawing Sheets

ENDOSCOPIC SUTURING DEVICE

This is a continuation-in-part of commonly assigned co-pending patent application Ser. No. 07/947,662 filed on Sep. 18, 1992.

BACKGROUND OF THE INVENTION

This invention relates to a medical device, particularly an endoscopic medical device, which is designed to facilitate the surgical procedures of tissue approximation and vessel ligation.

As medical and hospital costs continue to increase, surgeons are constantly striving to develop advanced surgical techniques. Advances in the surgical field are often related to the development of operative techniques which involve less invasive surgical procedures and reduce overall patient trauma. In this manner, the length of hospital stays can be significantly reduced, and therefore the hospital and medical costs can be reduced as well.

One of the truly great advances in recent years to reduce the invasiveness of surgical procedures is endoscopic surgery. Endoscopic surgery involves the use of an endoscope, which is an instrument permitting the visual inspection and magnification of any cavity of the body. The endoscope is inserted through a tube, conventionally referred to as a cannula, after puncture of a hole into the soft tissue protecting the body cavity. The hole is made with a trocar, which is a sharp-pointed instrument. The trocar includes an obturator, or cutting implement, which is slideably and removably disposed within a trocar cannula. The obturator will puncture a hole in the tissue equal in size to the inner diameter of the trocar cannula. After puncture, the obturator can be slideably withdrawn from the trocar cannula. The surgeon can then perform diagnostic and therapeutic procedures at the surgical site with the aid of specialized instrumentation designed to fit through the trocar cannula and additional trocar cannulas providing openings into the desired body cavity as may be required.

In many surgical procedures, suturing and ligating are required to close wounds. For example, suturing to approximate tissue, which requires the formation of a suture knot for placement of a stitch, is often required for proper healing of lacerations and surgical incisions. Additionally, ligating blood vessels to be cut within the surgical site is often necessary in numerous surgical procedures. The vessels may then be severed between the ligations. The primary reason for ligating the vessels is to maintain the surgical site free of an excess of blood and to reduce blood loss in the patient.

Conventionally, surgeons have closed blood vessels with ligatures, which are long, relatively straight strands of suture material. As is the case with the formation of a suture knot to place a stitch, the surgeon must manually tie a knot on the ligature after the ligature is looped around the vessel desired to be closed. Unfortunately, the formation of a knot on sutures and conventional ligatures is tedious and time-consuming during endoscopic surgical applications where a surgeon's manual operative techniques within the surgical site are severely restricted.

In more recent years, a ligature has been developed which is better adapted for endoscopic surgery. ENDOKNOT gut ligature is a device formed from a suture material of surgical catgut. The catgut ligature is securely fastened within a cannula at one end and attached to a needle at the other end. This device is described in the 1991 package insert for the product sold by Ethicon, Inc., which insert is entitled "ENDOKNOT Suture Made With Chromic Gut". Although ENDOKNOT gut ligature facilitates ligation of vessels through small incisions in bodily cavities, the surgeon is required to manually tie the ligature knot extracorporeally, i.e. outside the body, to ligate a vessel. This is a time consuming and laborious process, especially for inexperienced surgeons, and represents a significant disadvantage to the use of the ENDOKNOT ligature device during endoscopic surgery.

An improved device for ligation is described in European Patent Application 477,020, published Mar. 25, 1992. This device has a suture loop extending from the cannula. The loop is secured to the suture strand with a slip knot. This device eliminates the need to tie a knot extracorporeally, but the loop is extremely difficult to maneuver and position during endoscopy. In addition, it is difficult to avoid undesirably rotating the loop during use. Furthermore, the device is designed only for ligation, and not for tissue approximation as well.

A similar device to that described in the European patent application discussed above is disclosed in U.S. Pat. No. 5,129,912. This device has a pre-looped suture and needle for tissue approximation, and means for applying tension on the suture knot. Unfortunately, this device suffers from similar deficiencies because it too is difficult to maneuver and position during endoscopy.

Another attempt to avoid the need for manually tying the knot extracorporeally for ligation or tissue approximation is described in U.S. Ser. No. 728,443, filed Jul. 11, 1991. This reference describes a device which has a partially tightened knot secured around a cannula. The knot can be slid down the cannula onto a suture strand to make a loop which can then be subsequently tightened into a secure knot. Unfortunately, in operation the user must thread the suture strand up through the cannula before sliding the partially tightened knot down the cannula to make the loop. This threading operation is undesirable because it is time consuming and tedious. A similar device is shown in U.S. Pat. No. 2,012,776.

In view of the significant deficiencies of the prior art, an endoscopic suturing device having a suture loop which avoids manually tying knots extracorporeally, and is designed to easily manipulate and position the suture loop during use, would be highly desired within the medical community. Additionally, it would be highly desirable if such a design were designed which offered the flexibility for use to not only ligate vessels but also approximate tissue.

SUMMARY OF THE INVENTION

The invention is a medical device which comprises a cannula and a suture. The cannula has a proximal end and a distal end, and the distal end has a beveled surface thereon. The cannula also has a first channel extending axially through it, and a second channel extending from the beveled surface to the first channel.

The suture has a slide end, a distal loop, and a slip knot securing the loop to the slide end. The slide end is threaded through the first and second channels of the cannula, and protrudes from the proximal end of the cannula.

The device has means for securing the positioning of the slide end of the suture in the first channel of the cannula.

In a preferred embodiment, the suture has a stay end extending from the slip knot, and a needle attached to the stay end. In this manner, the device can be used for tissue approximation, or if desired, the needle can be detached and the device would then be especially well adapted for vessel ligation.

Surprisingly, the distal loop of the suture is easily manipulated and positioned during use. Therefore, the device is particularly suited for endoscopic surgery. The threading of the slide end of the suture through the first and second channels of the cannula helps to lock the distal loop of the suture in place, thus preventing or reducing any rotation of the loop during usage. This in turn greatly improves maneuverability in general of the device. Also, the distal loop of the suture can be easily placed at the desired surgical site.

Additionally, the beveled surface at the distal end of the cannula makes the distal end more visible and easy to locate during endoscopic surgery. The beveled surface serves as a platform to support the slip knot and to prevent any unwanted shifting when the device is used. Furthermore, the design of this device permits greater visibility of the slip knot as well when the device is being used.

Another aspect of the present invention is the above-described device wherein the cannula has a frangible proximal end to which the proximal end of the suture is mounted. The suture is manipulated by first breaking the frangible proximal end off from the cannula and then pulling on the broken-off proximal end and the suture.

DESCRIPTION OF THE PREFERRED EMBODIMENT

As used in this specification, the word "distal" is used to describe that portion of the device which extends away from the user during use, and the word "proximal" is used to describe that portion of the device that extends toward the user during use. Similarly, "distally" refers to movement extending away from the user during use of the device, and "proximally" refers to movement extending toward the user.

Figure 1:
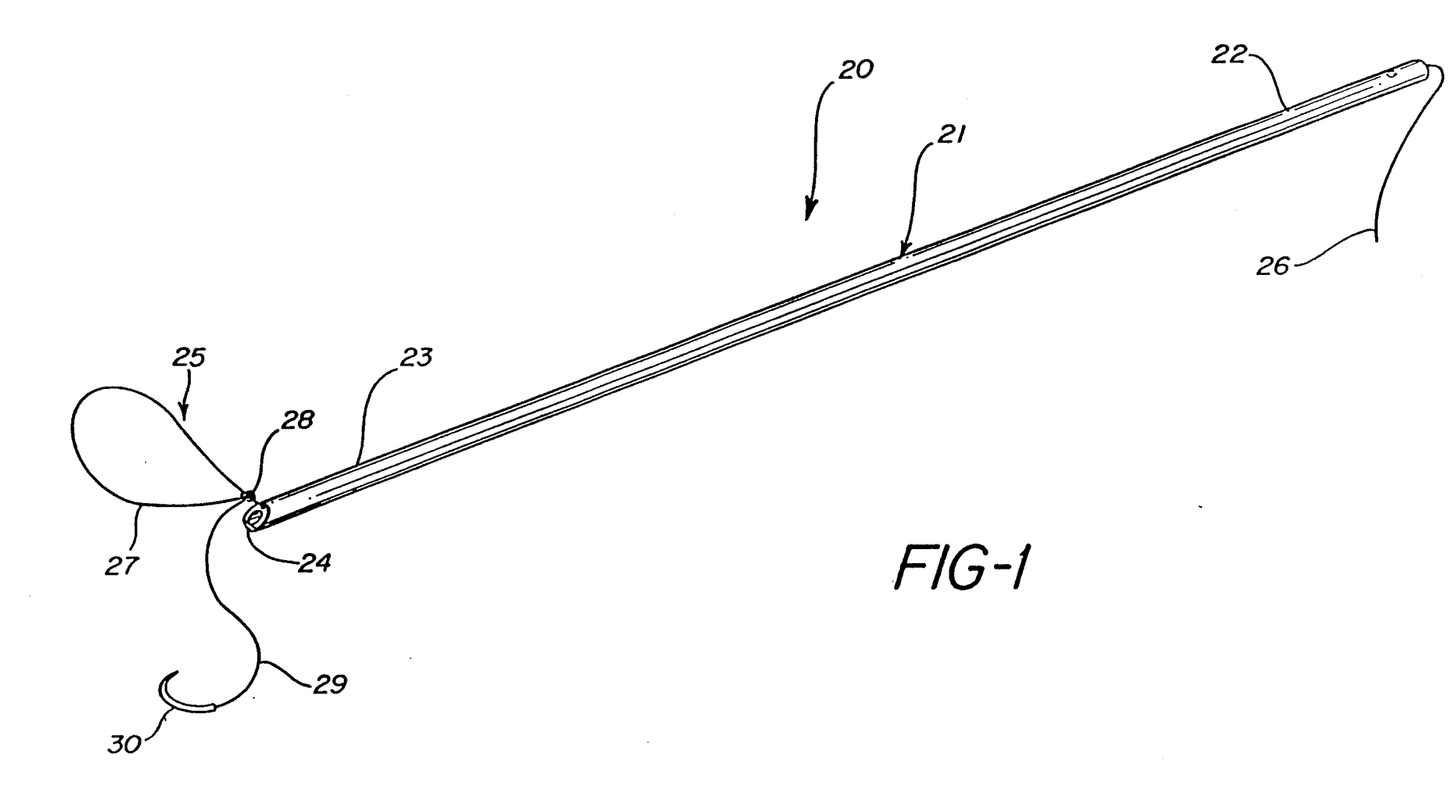
FIG. 1 is a perspective view of the preferred medical device of this invention.

Referring to FIG. 1, there is shown the preferred medical device 20. The device has a cannula 21 with proximal and distal ends 22 and 23, respectively. The distal end 23 of the cannula terminates with a beveled surface 24. The device also includes a suture 25. The suture has a slide end 26, a distal loop 27 and a slip knot 28. The slip knot secures the distal loop to the slide end of the suture. Extending from the slip knot is stay end 29 to which a surgical needle 30 is attached.

Figure 2:
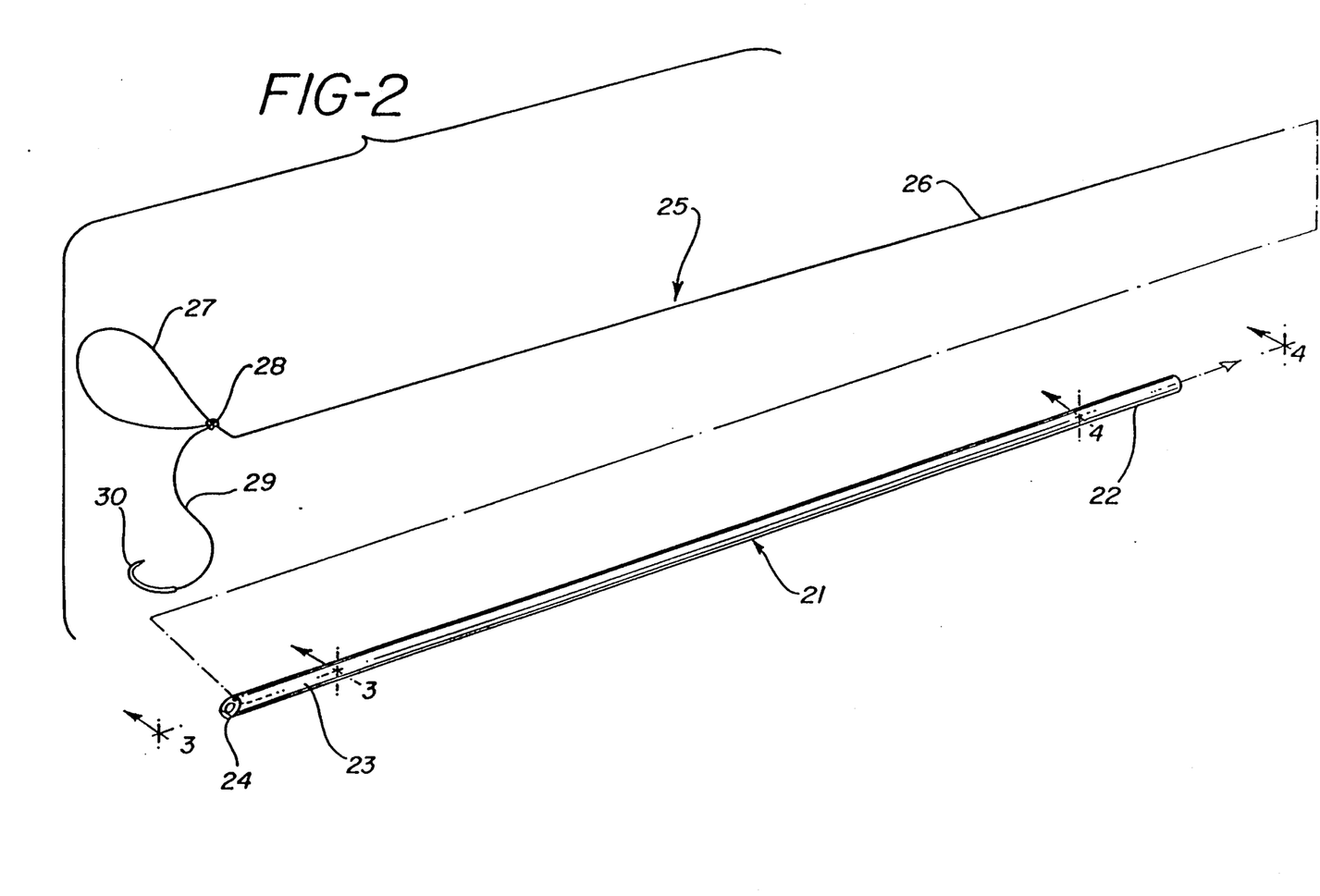
FIG. 2 is an exploded perspective view of the preferred medical device.

The incorporation of the suture 25 into cannula 21 to form the preferred device can be seen at FIG. 2. The slide end 26 of the suture is threaded completely through the cannula until the slip knot 28 makes contact with the beveled surface 24 of the cannula. The slide end is long enough so that it protrudes from the proximal end 22 of the cannula when the slip knot makes contact with the cannula. The secure positioning of the slide end of the suture in the first channel of the cannula is provided so that the portion of the slide end protruding from the proximal end of the cannula does not slide back into the cannula, as will be explained in more detail with respect to FIGS. 4 and 5.

The suture 25 can be composed of any surgical suture material. Suture materials can be composed of synthetic and nonsynthetic filaments, as well as absorbable and nonabsorbable fibers. Examples of suitable nonabsorbable suture materials include, but are not limited to, nylon, polypropylene, steel, and polyethyleneterephthalate (PET). The preferred sutures are synthetic bioabsorbable sutures. Examples of suitable bioabsorbable sutures are those which are derived from the polymerization of lactone monomers, e.g., lactide, para-dioxanone and ε-caprolactone.

The stay end 29 of the suture extending from slip knot 28 can be attached to the surgical needle 30 using standard needle attachment. Alternatively, it can be attached using removable or detachable needle attachment. In the case of standard needle attachment, the suture is securely attached to the needle and is not intended to be separated from the needle except by cutting or severing the strand. Removable needle attachment, by contrast, is such that the needle is separable from the strand in response to a force exerted by the surgeon, as illustrated, for example, in European Patent Application 0420605 and U.S. Pat. No. 3,926,194.

The configuration of slip knot 28 of the suture can be any configuration which allows for sliding movement of the slide end 26 of the suture proximally and prevents such sliding movement distally. In this manner, the slip knot serves to function as a knot which will allow for the continual reduction in the size of the distal loop 27 of the suture, yet prevents the enlargement of this distal loop, so that a secure and strong suture knot for approximating or ligating tissue can be formed.

The material of construction of the cannula 21 of the preferred device is not critical, so long as whatever material is chosen is sufficiently biocompatible with bodily tissue. A preferred material of choice for the cannula is nylon because of the ease with which it can be fabricated and its biocompatability.

Figure 3:
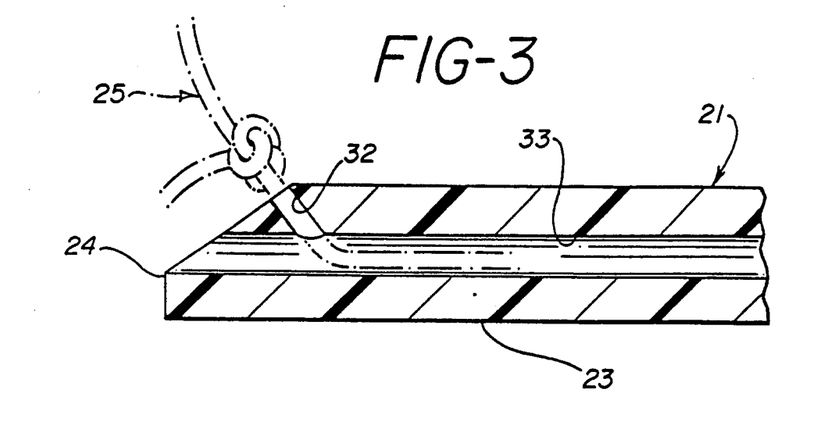
FIG. 3 is a cross-sectional view of the distal end of the cannula of the preferred medical device, taken along line 3—3 of FIG. 2, prior to threading the slide end of the suture through the first and second channels of the cannula.

The slide end of the suture is threaded through first and second channels in the cannula. Referring now to FIG. 3, the slide end of the suture would first be threaded through second channel 32 of the cannula, and then subsequently through first channel 33. The first channel 33 is the primary channel of the cannula, and extends axially completely through the cannula from the distal to the proximal end. The second channel 32 extends from the beveled surface 24 of the cannula to the first channel so that what in effect is formed is a continuous opening in the cannula from the beveled surface to the proximal end of the cannula. The angle between the first and second channels is preferably no less than about 20°, but ideally it is about 30°. Likewise, the angle between the beveled surface and the first channel is preferably no less than 20° but ideally it is about 30°. When the slide end of the suture is threaded through the first and second channels of the cannula, the slip knot of the suture abuts the opening of the second channel at the beveled surface, and the slide end protrudes from the proximal end of the cannula.

Figure 4:
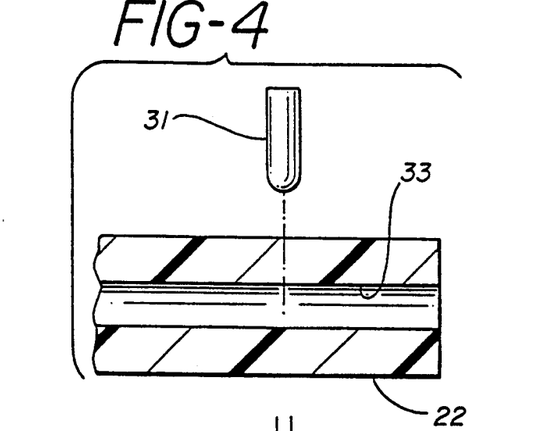
FIG. 4 is a cross-sectional view of the proximal end of the cannula of the preferred device, taken along line 4—4 of FIG. 2, prior to threading the slide end of the suture through the first and second channels of the cannula.
Figure 5A:
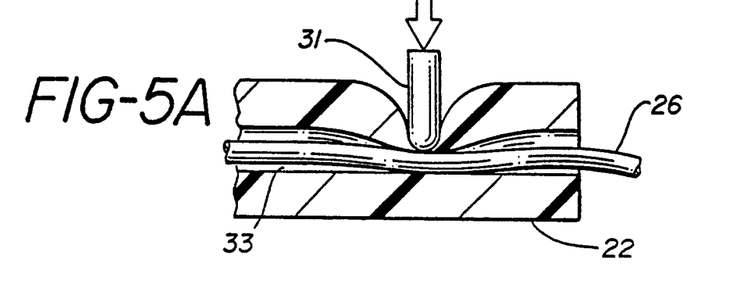
FIGS. 5A and 5B are views similar to that of FIG. 4 showing the preferred means for securing the positioning of the slide end of the suture in the first channel of the cannula of the preferred device.
Figure 5B:
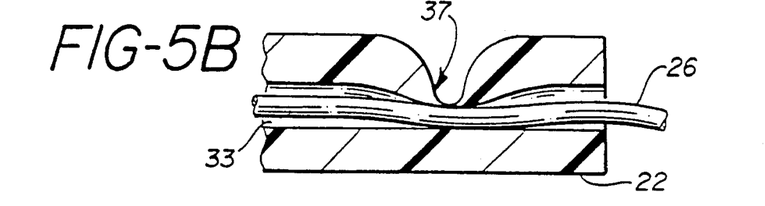

The creation of a partial obstruction in the first channel of the cannula at its proximal end to provide for secure positioning of the slide end of the suture during packaging and routine handling is illustrated in FIGS. 4 and 5. After the slide end of the suture is threaded through the first and second channels of the cannula, a metallic blunt-tipped pin 31 is heated to a temperature above the melting temperature of the cannula, and the heated pin is pressed against the proximal end 22 of the cannula. The pressure of the heated pin is applied in a direction substantially perpendicular to the longitudinal axis of the cannula. The heated pin, upon contact with the cannula, causes the contacted area of the cannula to melt, thus forming a hole in the outer surface of the cannula through which the pin can be inserted into the first channel. The pin is then inserted partially into the first channel to cause a protrusion 37 extending into the first channel. The cross-sectional inner diameter at this region of the first channel of the cannula is less than that of the remainder of the first channel. This protrusion in turn creates a partial obstruction in the pathway that the slide end of the suture must take if it were pulled through the first channel of the cannula. In this manner, the slide end is prevented from sliding back inside the cannula. However, the partial obstruction caused by the protrusion does not prohibit the surgeon from pulling the slide end protruding from the cannula in the proximal direction when the device is used during surgery. Once the protrusion is created with the pin, the pin is then removed from the cannula.

The depth to which the pin is inserted may create minimal contact between the blunt-tipped surface of the pin and the suture, although this contact may be unnecessary to provide for the proper securement of the positioning of the slide end inside the cannula. The protrusion which the pin creates stabilizes the suture so that it is prevented from sliding freely upon routine handling, yet only creates a slight drag when the user pulls the suture to close the loop and tighten the knot, as will be explained in more detail with reference to FIGS. 7-12. When the pin is removed from the cannula, the protrusion created from the contact with the pin will solidify upon cooling, and therefore cause a permanent obstruction in the first channel of the cannula.

Figure 6:
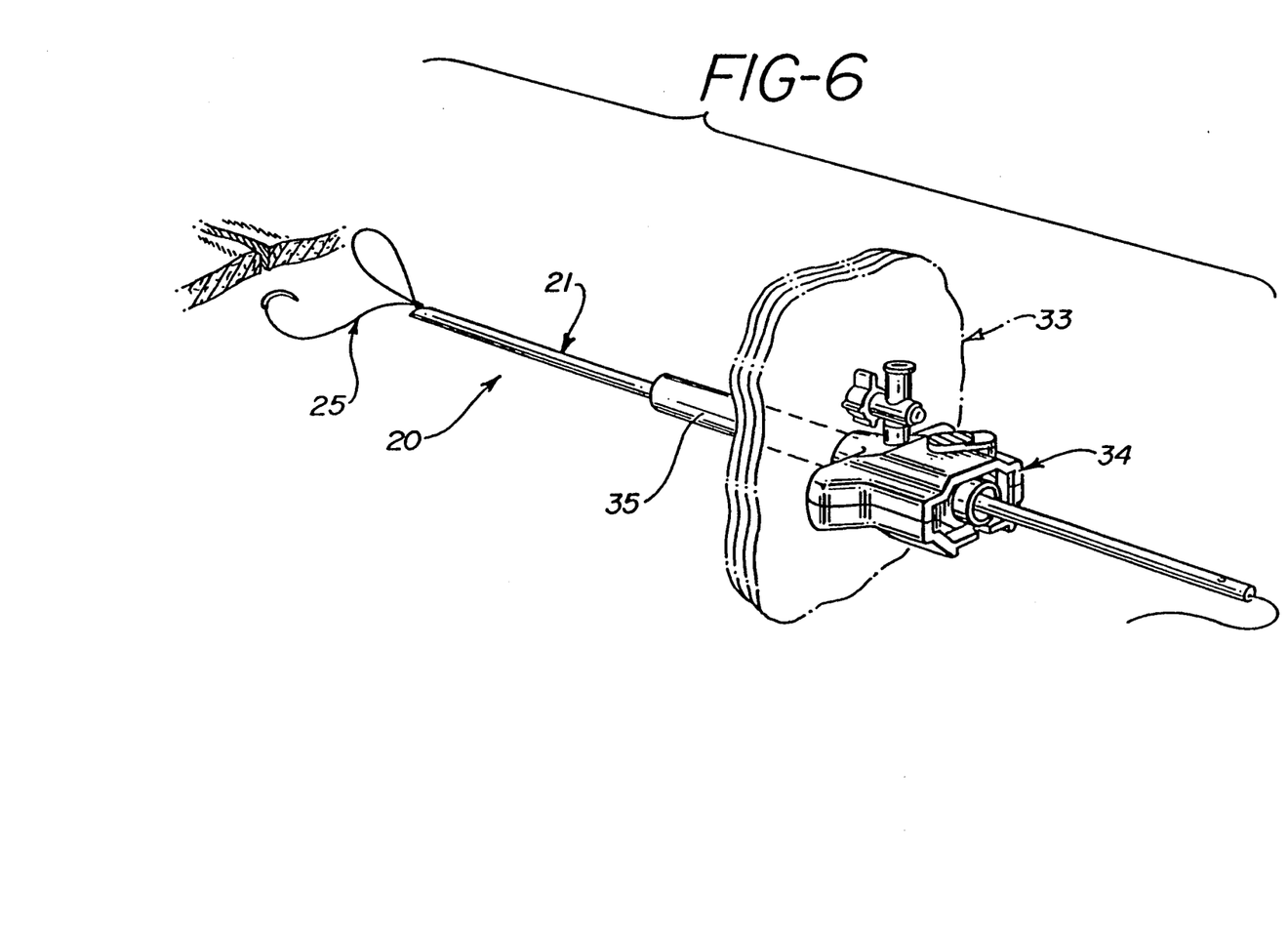
FIGS. 6–12 are perspective views showing the recommended sequence of steps for endoscopically approximating tissue using the preferred medical device of this invention.
Figure 7:
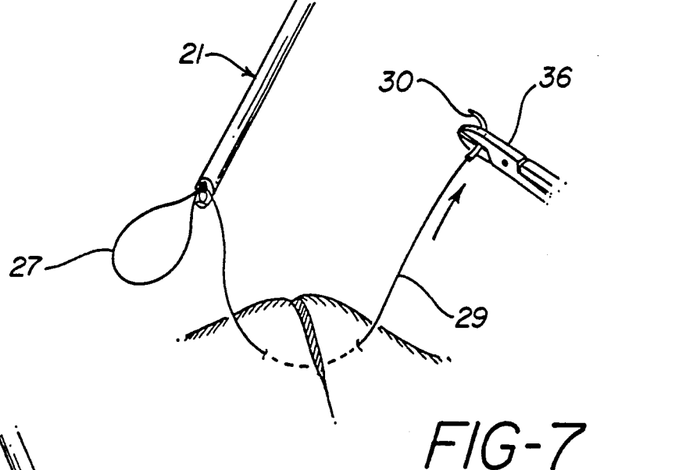
Figures 8, 9:
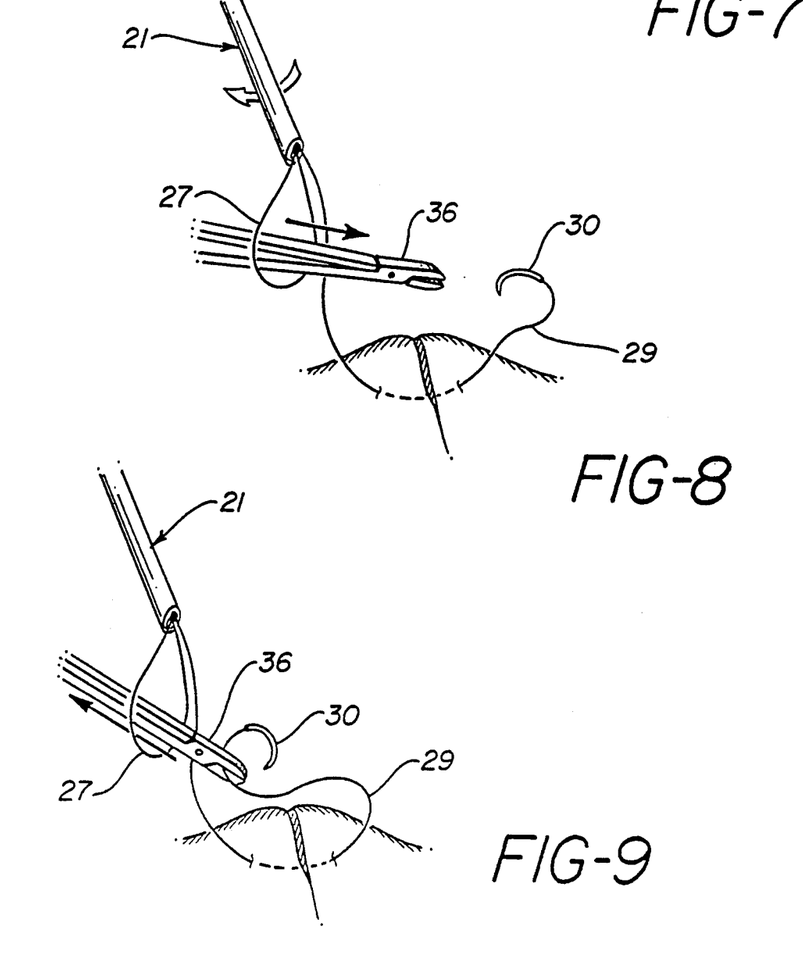
Figure 10:
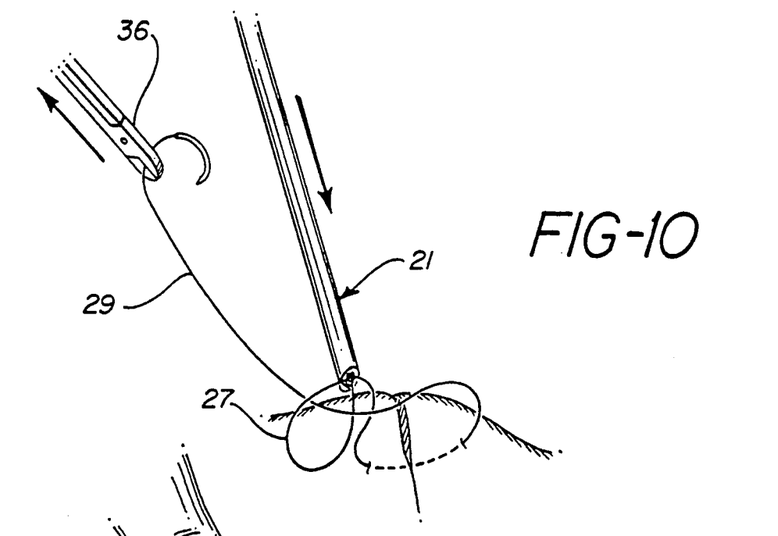
Figure 11:
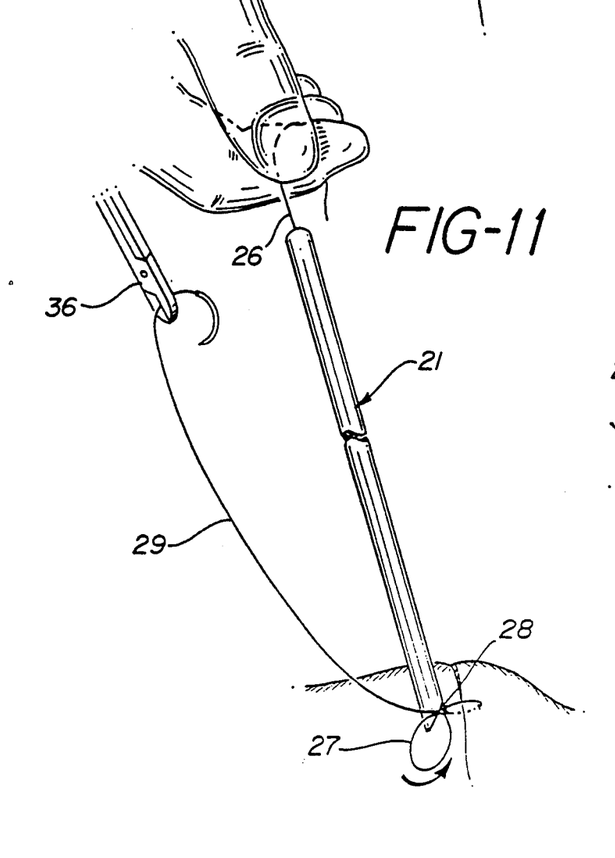
Figure 12:
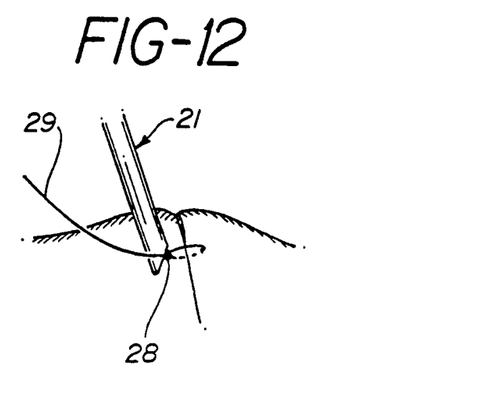

To approximate tissue using the device, the surgeon would ideally first backload the cannula of the device into and through an appropriate introducer for a trocar. The introducer, with the device loaded into it, is then placed into an appropriately sized trocar. The trocar provides access into a body cavity where the desired tissue approximation is to occur. As illustrated in FIG. 6, the cannula 21 of the medical device 20 is pushed into the field of surgery through trocar 34 and trocar cannula 35, which have penetrated bodily tissue 33.

Referring now to FIGS. 7-12 in sequence, the surgeon would use graspers 36 to hold and orient the needle, and to pass the surgical needle through the two segments of tissue to be joined. The surgeon then positions distal loop 27 of the suture by rotating the cannula 21 of the device so that the graspers can be easily passed through the distal loop. Once the graspers have been passed through the distal loop, the surgeon then grasps the stay end 29 of the suture just behind the needle, and pulls the stay end and needle of the suture through the loop. As the stay end of the suture is pulled, the cannula 21 is simultaneously advanced distally until the base of the slip knot lies against the tissue to be joined. While holding the stay end of the suture firmly, the distal loop 27 of the suture can now be closed to form the suture knot. To close the loop, that portion of the slide end of the suture protruding from the proximal end of the cannula is held firmly and pulled proximally. As the slide end is pulled proximally, the distal loop subsequently becomes smaller and smaller until it is cinched about the suture to form a knot joining the severed tissue. Once the knot is formed, excess suture at the stay end and the slide end can be easily removed, and the needle, excess suture and cannula can be removed from the surgical site.

The method of using the device for ligation is substantially the same as the method described above for tissue approximation. The only significant difference is that the surgeon would first remove the needle from the suture prior to inserting the device into and through the trocar. The needle is generally unnecessary for ligation because the suture can merely be looped around the vessel desired to be ligated. This looping procedure can be preformed without penetrating tissue, so that the needle can be removed without affecting the ease with which the ligation can be preformed.

Figures 13, 14, 15:
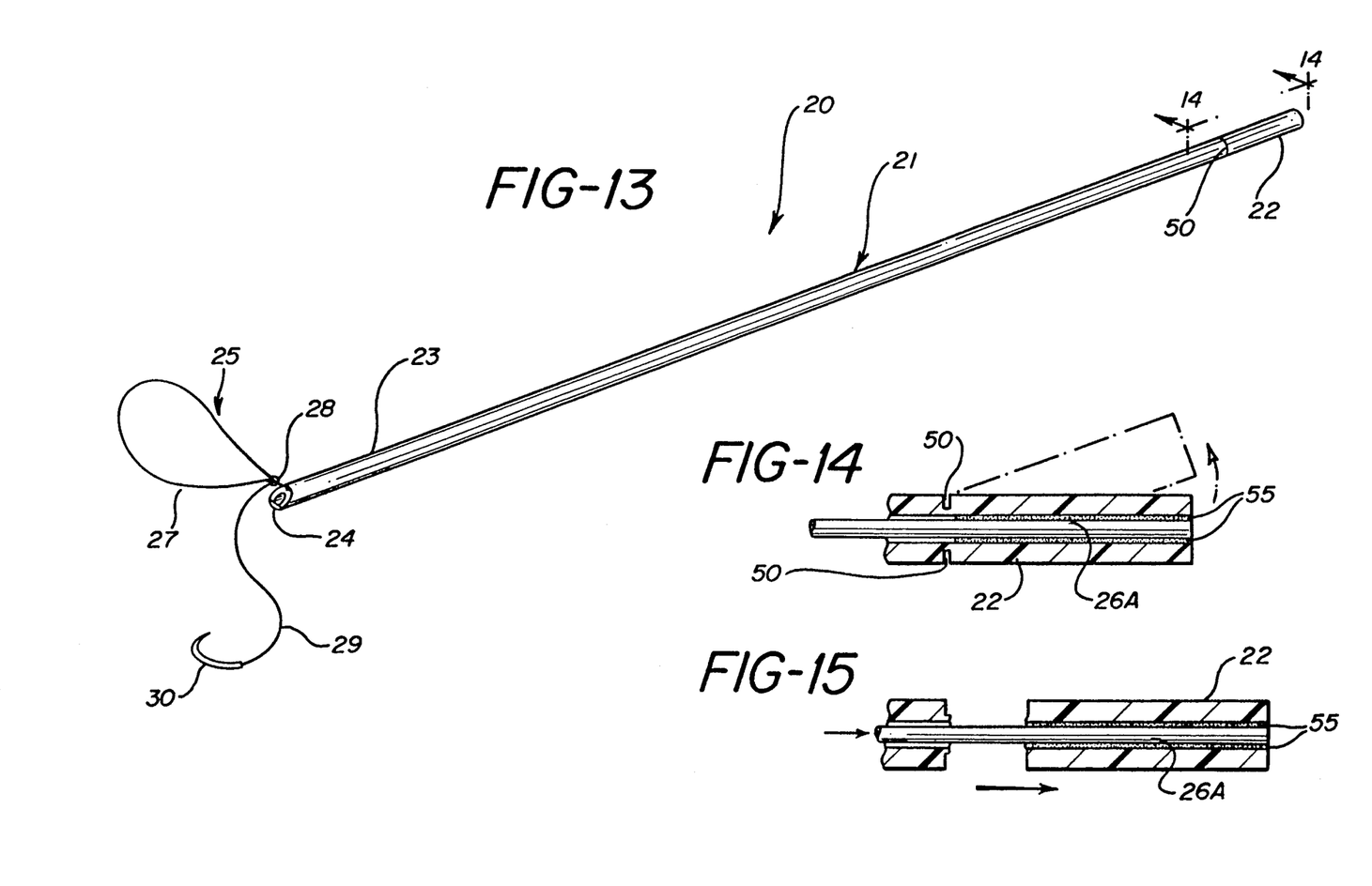
FIG. 13 is a perspective view of a medical device of the present invention having a cannula with a frangible proximal end.
FIG. 14 is a partial cut-away view along view line 14—14 of FIG. 13, showing the frangible proximal end of the cannula prior to breaking off the end.
FIG. 15 is a partial perspective view of the proximal end of FIG. 14 showing the frangible proximal end broken away from the proximal end of the cannula.

Referring to FIGS. 13-18, an alternate embodiment of the device 20 of the present invention is seen. Specifically, the device 20 is seen to have a cannula 21 having a frangible proximal end 22. Score line 50 is seen to separate frangible proximal end 22 from the remainder of the cannula 21. The proximal end 26A of suture 25 is seen to be mounted in frangible end 23 as seen in FIGS. 14, 15, 17 and 18. The proximal end 26A may be mounted in the frangible proximal end 22 by conventional methods including mechanical fasteners bonding agents such as glues, cements, adhesives and the like and equivalence thereof. Referring to FIG. 14, it is seen that the proximal end 26A of suture 25 is mounted in place with a conventional bonding agent 55.

Figure 17:
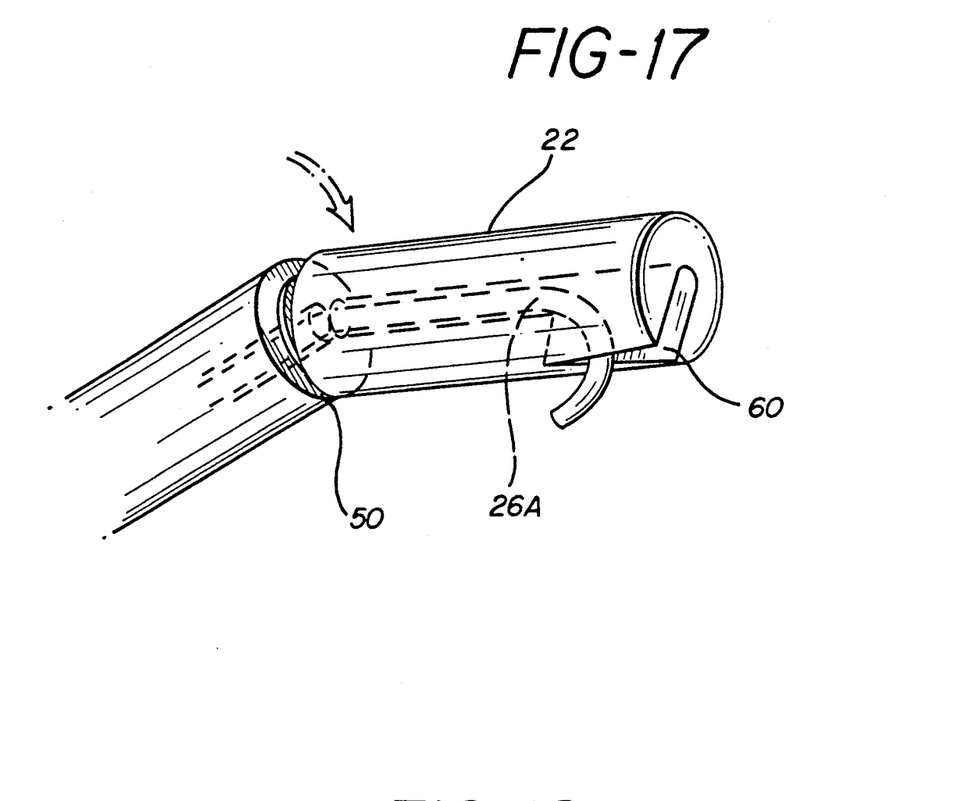
FIG. 17 is partial perspective view of the distal end of the cannula showing the distal end partially broken away from the cannula along the score line and also showing a V-shaped notch for mounting and retaining the proximal end of the suture in the frangible proximal end.
Figure 18:
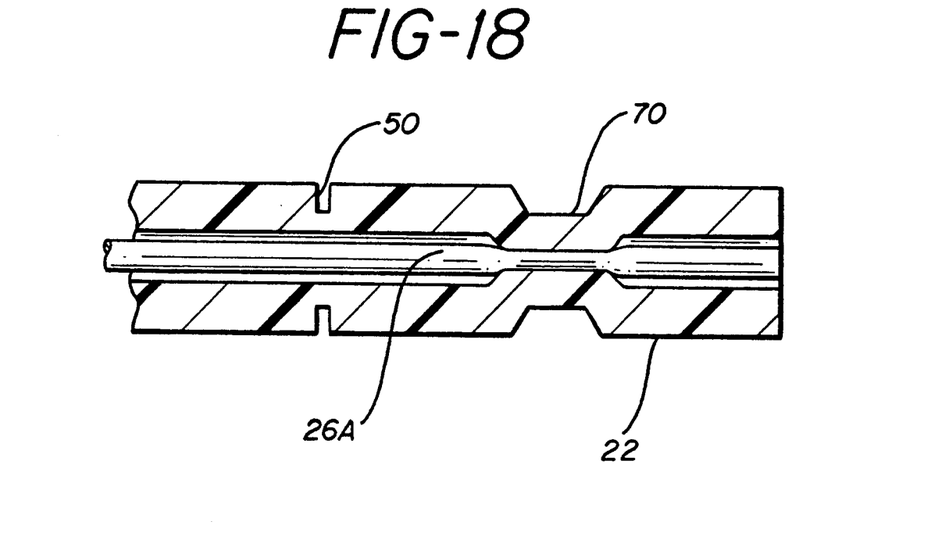
FIG. 18 is a partial cross-sectional view of the proximal end of the cannula showing the score line and showing an alternate suture mounting embodiment wherein the suture is crimped in place in the frangible proximal end.

Referring to FIGS. 17 and 18, it can be seen that the proximal end 26A of suture 25 can be mounted in conventional manners in frangible proximal end 22 including inserting the proximal end 26A into a V-shaped notch 60 or crimping the proximal end 26A with a crimp 70.

Figure 16:
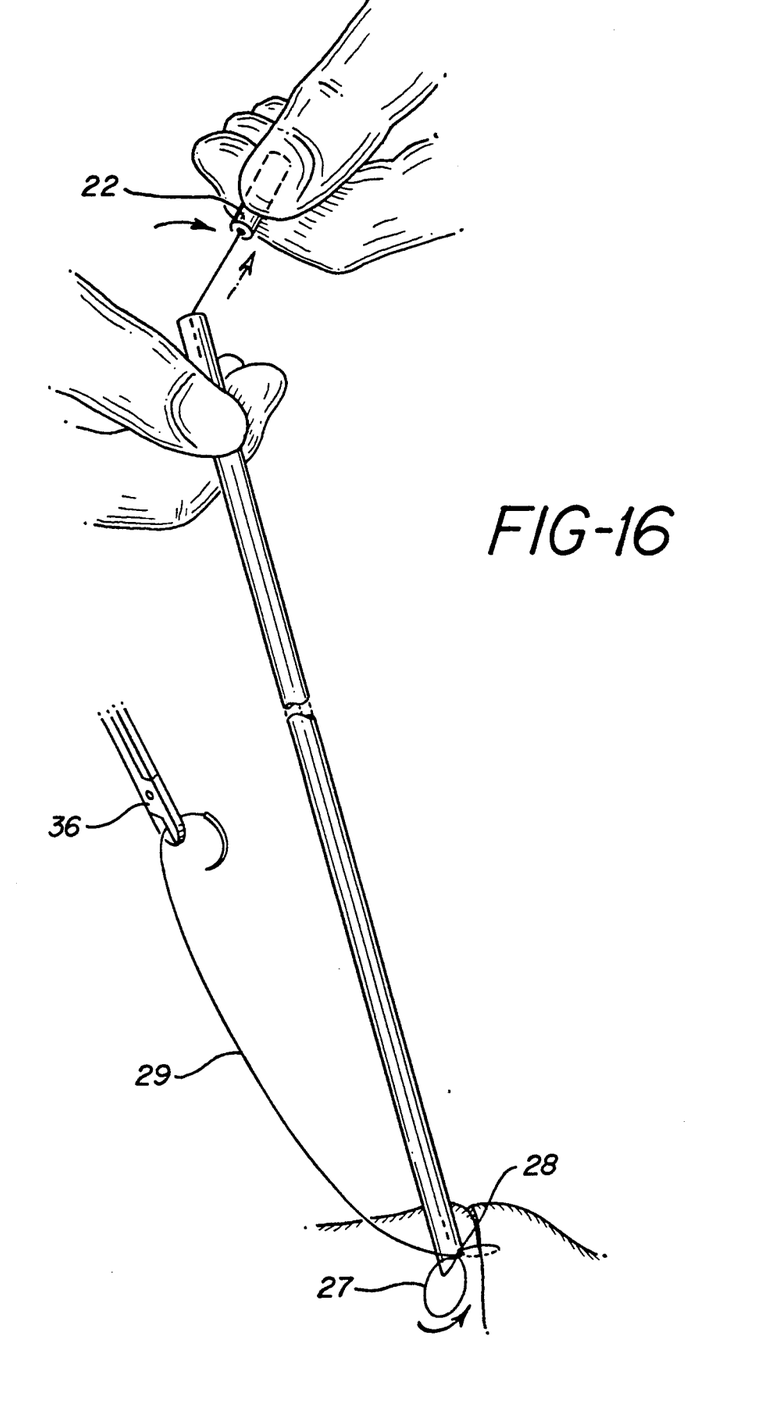
FIG. 16 is a perspective view the medical device of the present invention during use showing the frangible proximal end broken away from the cannula and pulled along with the suture during an endoscopic surgical procedure in order to close the suture loop.

Referring to FIGS. 14, 15 and 16, the device 20 is used in a manner as previously described with the exception that the proximal end 23 is rotated sufficiently about score line 50 to effectively cause the proximal end 22 to break away from the cannula 21 about the score line 50. Then the frangible proximal end 22 and the proximal end 26A of the suture 25 which is mounted in the interior passage of frangible proximal end 22 are pulled by the surgeon in order to close the suture loop 27 and the device is used in a manner similar to that described above. The score line 50 can be placed into the proximal end of the cannula 21 in conventional manners including conventional cutting apparatus and the like or by molding the score line 50 into the cannula 21.

Although this description has focused on the preferred embodiment of the device, it is readily apparent that numerous additional embodiments of the device can be envisioned without departing from the spirit and scope of the claimed invention.

We claim:

1. A medical device comprising:
   a) a cannula, said cannula having a distal end and a frangible proximal end, said distal end having a beveled surface thereon, said cannula having a first channel extending axially therethrough and a second channel extending at an angle from said beveled surface to said first channel, said cannula having a score line adjacent to the slide end;
   b) a suture, said suture having a proximal end, a distal loop, and a slip knot securing said loop to said slide end, said slide end threaded through said first and second channels, and mounted to the proximal end of said cannula; and
   c) means for mounting the proximal end of said suture to the frangible proximal end.

2. The device of claim 1 wherein said suture has a stay end extending from said slip knot, and a needle attached to said stay end.

3. The device of claim 2 wherein said slip knot abuts the opening of the second channel at the beveled surface.

4. The device of claim 3 wherein said slip knot is configured to allow sliding movement of said slide end proximally so as to continually reduce the size of said distal loop.

5. The device of claim 4 wherein said means is a protrusion extending partially into said first channel.

6. The device of claim 5 wherein the angle between said first and second channels is about 30°.

7. The device of claim 1 wherein the means for mounting the proximal end of the suture in the frangible proximal end of the cannula comprises an adhesive.

8. The device of claim 1 wherein the means for mounting the proximal end of the suture in the frangible proximal end of the cannula comprises a V-shaped notch in the frangible proximal end.

9. The device of claim 1 wherein the means for mounting the proximal end of the suture in the frangible proximal end comprises a crimp in the frangible proximal end.

* * * * *